US005698413A

United States Patent [19]
Hollingshead

[11] Patent Number: 5,698,413
[45] Date of Patent: Dec. 16, 1997

[54] METHOD OF EVALUATING CHEMOTHERAPEUTIC AGENTS IN VIVO

[75] Inventor: Melinda G. Hollingshead, Knoxville, Md.

[73] Assignee: The United States of America as represented by the Department of Health and Human Services, Washington, D.C.

[21] Appl. No.: 58,154

[22] Filed: May 5, 1993

[51] Int. Cl.$^6$ .............................. C12Q 1/18; C12N 5/00; A61F 13/00

[52] U.S. Cl. ..................... 435/32; 435/182; 435/240.1; 435/240.22; 435/240.242; 424/422; 424/423; 424/424; 264/4; 264/4.7

[58] Field of Search ..................... 435/32, 182, 240.1, 435/240.22, 240.242; 424/422, 423, 424; 264/4, 4.7

[56] References Cited

U.S. PATENT DOCUMENTS

| | | | |
|---|---|---|---|
| 4,324,683 | 4/1982 | Lim et al. | 264/4 |
| 4,352,883 | 10/1982 | Lim | 435/182 |
| 4,353,888 | 10/1982 | Sefton | 424/424 |
| 4,409,331 | 10/1983 | Lim et al. | 435/178 |
| 4,495,288 | 1/1985 | Jarvis et al. | 435/241 |
| 4,892,538 | 1/1990 | Aebischer et al. | 424/424 |
| 5,416,022 | 5/1995 | Amiot | 435/284 |

FOREIGN PATENT DOCUMENTS

| | | |
|---|---|---|
| 2065662 | 3/1993 | Canada . |
| 0218400 | 4/1987 | European Pat. Off. . |
| 2073007 | 9/1971 | France . |
| 8904655 | 1/1989 | WIPO . |
| 9115245 | 10/1991 | WIPO . |

OTHER PUBLICATIONS

Christenson et al, (1992) "Biomedical Applications of Immobilized Cells" *Fundamentals of Animal Cells Encapsulation and Immobilization* (MFA Gussen, ed.), CRC Press, Boca Raton, Florida.
Bagtas et al. (1991) "A Novel Rapid In Vivo Chemosensitivity Assay", *Proceeding of the American Association for Cancer Research*, May 15–18, 1991 Houston, Texas Abstract #2256.
Lipsky et al. (1993) "A rapid in vivo therapeutic assay for human carcinomas", *Proceeding fo the American Association for Cancer Research*, Mar. (1993), Houston, Texas Abstract #1784.
Chu et al. (1991) "In vivo assessment of therapy on human carcinomas transduced with STK gene", *Proceedings of the American Association for Cancer Research*, Mar. (1993) Houston, Texas, Abstract #2008.
Spectrum Catalog (1991–1992), "Preparative Molecular Products for the Third Millennium", pp. 185, 186, 203.
C.K. Colton, et al. (May 1991) "Bioengineering in Development of the Hybrid Artical Pancreas", *Journal of Biomechanical Engineering*, May (1991), vol. 113.
Christenson, Lisa (May 1990) "Polymer Encapsulate Thymic Stromal Tissue: Biocompatability, Procurement and Functional Studies", Doctoral in the Division of Biology and Medicine at Brown University, (May 1990) Chapter 1.
TSI Corporation Press Release, Jan. 13, 1992.
Christenson, et al. (1992), "Biomedical Applications of Immobilized Cells", *Fundamentals of Aminal Cell Encapsulation and Immobilization*. (MFA Gussen, ed), CRC Press, Boca Raton, Florida.
X.Q. Li et al., Antiviral Research, vol. 10, No. 4, 5, (1988), pp. 179–191 "A New in Vivo Anti–Viral Assay Using Microencapsulated Infected Cell Cultures".
J.M. Hwang, et al., Chinese Medical Journal (Taipei), vol. 51, No. 3, Mar. (1993), pp. 166–175 "A New in Vivo Assay of the Reactions of Microencapsulated Human Tumor Cells to Chemotherapeutic Drugs".
C.F. Chen et al., Proceedings of the National Science Council, Republic of China, vol. 12, No. 4, (1988), pp. 252–261 "Microencapsulation of Tumor Cells and Assay for Selecting Anticancer Drugs".
J. McMahon et al., Journal of the National Cancer Institute, vol. 82, No. 22, (1990), pp. 1761–1765 "Feasibility of Cellular Microencapsulation Technology for Evaluation of Anti–Humanimmunodeficiency Virus Drugs in Vivo".
Hollingshead, et al., Proceedings of the 84th Annual Meeting of the American Association for Cancer Research, vol. 34 (Mar. 1993), Abstract #2562, "Short Term in Vivo Cultivation of Human Tumor Cell Lines for Assessing Preventive Chemotherapeutic Agents".
Jauregui et al, "Hybrid Artificial Liver" Chapter 39, In Szycher, M. (Ed.), *Biocompatible Polymers, Metals, and Other Composition Composites* (Lancaster, PA, Technomic Pub) 1983, pp. 907–928.
Gorelik et al, *Cancer Research*, vol. 47, pp. 5739–5747, Nov. 1, 1987.
Lacy et al, *Science*, vol. 254, pp. 1782–1784, Dec. 1991.
Dieter et al, *Leukemia Research*, vol. 13, No. 9, pp. 841–849, 1989.
Colton et al, *Journal of Biochemical Engineering*, vol. 113, pp. 152–170, May 1991.
Shockley et al, *Ann. N.Y. Acad. Scii*, pp. 367–382, 1991.
Selby et al, *Cancer Research*, vol. 42, pp. 4758–4762, 1982.
Allen et al, *Antimicrobial Agents and Chemotherapy*, vol. 36, pp. 206–208, 1992.
Selby, P.J. et al., "Use of the Agar Diffusion Chamber for the Exposure of Human Tumor CElls to Drugs," *Cancer Research*, 42:4758–62 (1982).
Allen, L.B. et al., "Novel Method for Evaluating Antiviral Drugs Against Human Cytomegalovirus in Mice," *Antimicrobial Agents and Chemotheraphy*, 36:206–208 (1992).

*Primary Examiner*—Cecilia J. Tsang
*Assistant Examiner*—Abdel A. Mohamed
*Attorney, Agent, or Firm*—Morgan & Finnegan L.L.P.

[57] ABSTRACT

The present invention relates to a method of screening chemotherapeutic agents in vivo. The method comprises implanting into a laboratory animal a biocompatible, semipermeable encapsulation device containing a target cell-line, treating the laboratory animal with a test agent, then evaluating the target cells for reaction to the test agent.

28 Claims, No Drawings

METHOD OF EVALUATING CHEMOTHERAPEUTIC AGENTS IN VIVO

FIELD OF THE INVENTION

The present invention relates to a method of screening chemotherapeutic agents in vivo using target cells grown in biocompatible, selectively permeable macrocapsules.

More particularly, the present invention involves a method for providing a retrievable sample of syngeneic, allogenic or xenogeneic cells into laboratory animals using cells or cell lines grown in selectively permeable hollow fibers or dialysis tubing. Following in vivo culture, with or without chemotherapeutic treatment, the cells are retrieved for in vitro evaluation of cell viability, cell density, cell growth potential, virus burden or other parameters appropriate for the test system.

BACKGROUND OF THE INVENTION

The desire for effective treatment against tumor growth and viral infection has created a need in the research and medical communities for a quick and reliable way to screen potential chemotherapeutic agents. That different types of tumor cell lines (e.g., renal, colon, pancreatic, etc.) react at different degrees to various chemotherapeutic agents, forces one to perform individual experiments usually screening one possible agent against one type of target cell or cell line.

For several years, this type of screening experiment was performed in vitro. For example, human tumor cells would be grown in semisolid media, a potential chemotherapeutic agent would be introduced into the media, and the viability of the cells after exposure would be measured. (See, Roper, P. R., and Drewinko, B., "Comparison of in vitro methods to determine drug-induced cell lethality", Cancer Res., vol. 36, pp. 2182–88 (1976)). However, the exposure of cells to drugs in vitro is highly artificial and restricts the use of drugs which require metabolic activation. It is doubtful whether such in vitro drug exposure can accurately reflect in vivo pharmacokinetics.

This led some researchers to develop ways in which to test possible chemotherapeutic agents in vivo. These models consist of implanting tumor cells into a laboratory animal, treating the animal with a possible chemotherapeutic agent, and then monitoring the animals to determine the effects of treatment on tumor growth. Several models were attempted, for example: (1) the subcutaneous tumor model which consists of surgically placing live tumor cells under the skin of a laboratory animal; (2) the subrenal tumor model, which measures the growth of tumor cells surgically implanted under the kidney capsule of laboratory animals; (3) the peritoneal model, in which the tumor cells are injected directly into the peritoneal cavity; and (4) the metastasis model, in which the primary tumor cells are injected into the foot of the laboratory animal.

These models are limited, however, because they only permit one type of tumor cell or cell line to be screened per experiment (per animal), which translates into the need for more test agent to screen several tumor lines. Furthermore, the animals need to be sacrificed to collect the tumor cells, and there is no way to control the effects of interaction between the tumor cells and the host laboratory animal.

Another model, which attempted to overcome these hurdles, is the agar diffusion chamber (Selby, P. J. et al., "Use of the Agar Diffusion Chamber for the Exposure of Human Tumor Cells to Drugs", Cancer Res., Vol. 42, pp. 4758–4762 (1982)). This method involves suspending tumor cells in agar, then introducing the suspended cells into a diffusion chamber. The diffusion chamber is then implanted into the peritoneal cavity of a laboratory animal, which is treated with a test agent. This method, however, suffered from the admitted drawbacks of being "labor-intensive and expensive" (Selby, p. 4761), as well as only permitting the implantation of one cell type or line because of the size of the diffusion chamber, and the presence of agar in the chamber.

Because of these drawbacks in the above in vivo models, a need still existed for a method of screening chemotherapeutic agents in vivo which was rapid, inexpensive, and which could be used to screen more than one cell line per experiment. The present invention satisfies this need by providing a method of screening test agents in vivo, involving the encapsulation of target cells in a device comprised of a biocompatible semipermeable membrane, and implantation of the device (subcutaneously, intraperitoneally, or intra-organ) in a laboratory animal which is then treated with the test agent.

Encapsulation of cells has been described in the art for a variety of purposes. For example, Lacy, P. E. et al., "Maintenance of Normoglycemia in Diabetic Mice by Subcutaneous Xenografts of Encapsulated Islets", Science, vol. 254, pp. 1782–1784 (1991), describes the use of hollow fibers fabricated from an acrylic copolymer to encapsulate small numbers of rat islet cells that were then transplanted into mice. The encapsulation device prevented an immune response against the rat islet cells, and permitted diffusion of the bioactive compound insulin to maintain normoglycemia in mice. (See, also, Colton, C. K. et al., "Bioengineering in Development of the Hybrid Artificial Pancreas", J. Biomech. Eng., vol. 113, pp. 152–170 (1991)).

In addition, U.S. Pat. No. 4,324,683 and U.S. Pat. No. 4,352,883 to Franklin Lim both teach and describe encapsulation of biological material in spherical microcapsules. The microencapsulation techniques taught by these patents, however, have several limitations. First, their microencapsulation techniques generate aerosols which produce a biohazardous condition if the materials being encapsulated pose a health risk by aerosol transmission. Second, their microcapsules are extremely difficult to recover in toto from the host animal. Third, only the intraperitoneal implantation site is feasible if recovery of the implant is desired. And finally, it is difficult to recover the encapsulated cells without contamination by host cells. These limitations have been circumvented in the present invention.

Shockley, T. R. et al., "Penetration of Tumor Tissue by Antibodies and Other Immunoproteins", Ann. N.Y. Acad. Sci., pp. 367–382 (1991) discusses preliminary experiments to examine the feasibility of using the hollow fiber model for in vivo experiments. Shockley, however, does not teach or suggest using a hollow fiber system to test antiviral, antibacterial, and antiparasitic drugs in vivo. Shockley further does not teach or suggest that the hollow fiber system can be used to test a single drug against multiple tumor or cell lines. It has not previously been shown that the hollow fiber system may be used to test a single drug against multiple cell lines in a single mammal.

Finally, Allen, L. B. et at., "Novel Method for Evaluating Antiviral Drugs against Human Cytomegalovirus in Mice", Antimicrobial Agents and Chemother., vol. 36, pp. 206–208 (1992), teaches a virus-host cell system in which human cytomegalovirus-infected human cells are entrapped in agarose plugs and cultivated in vitro or implanted into conventional mice. This system, however, is ineffective for encapsulation and implantation into mice of tumor cells or cells expressing a retrovirus such as HIV, because those cells will not replicate in the agarose concentrations of 1–1.5% taught by Allen.

All references cited and discussed above are herein incorporated by reference.

Despite the fact that microencapsulation and hollow fiber systems are known as described in the references cited above, the art still lacks a method for screening chemotherapeutic agents against one or more cell lines encapsulated in biocompatible, semi-permeable macrocapsules and implanted in a single mammal.

Accordingly, an object of this invention is to provide a method wherein a cell, cell line or infectious agent is encapsulated in a biocompatible, semi-permeable device and implanted into a mammal, which is then treated with a chemotherapeutic agent intended to affect the encapsulated cell or infectious agent.

An additional object of this invention is to provide a method wherein multiple types of cells or infectious agents can be cultured simultaneously in a single mammal so that evaluating experimental chemotherapeutic agents does not require as much of said agent as has been historically required.

A further object of this invention is to provide a method wherein a single experimental animal can carry implants in multiple sites allowing simultaneous evaluation of a chemotherapeutic agent's capacity to reach various physiologic compartments (i.e., subcutaneous, intraperitoneal and intra-organ).

SUMMARY OF THE INVENTION

In accordance with these and other objects of the present invention, a method of evaluating a chemotherapeutic agent using cells grown in a biocompatible, semi-permeable device in vivo is provided. The present method comprises providing a target cell or cells which are cultivated in vitro in medium appropriate for the cell line. Generally, a 10–20% serum concentration is recommended for cell lines which are routinely cultivated in serum-containing medium. Cells are collected, viability determined, and the cell density adjusted as needed for filling an encapsulation device.

After preparation, the cells are instilled into the encapsulation device. For the practice of the present invention, the encapsulation device is preferably a hollow fiber or dialysis tubing comprised of a biocompatible, semi-permeable material. After filling, the encapsulation device(s) is (are) implanted directly into a laboratory animal, or the samples are incubated for a period of time to allow stabilization of cell growth before implantation. Each recipient animal can receive a single implant at a single site or can receive multiple implants at multiple sites.

The laboratory animal is then treated with the test chemotherapeutic agent on a dose and schedule appropriate for the agent being evaluated. The implanted samples are allowed to remain in the host animal for an appropriate period of time, sufficient to permit the test agent to affect the target cells. The period of time varies for each test agent, and is preferably between 1 and 10 days. The implanted samples are then harvested for evaluation of the effects of the chemotherapeutic agent (called the endpoint).

This method provides a rapid and effective way in which to evaluate the efficacy of chemotherapeutic agents against one or more target cells at one or more implant sites by comparing the endpoint results obtained in animals treated with the test agents to the results obtained in animals treated with a placebo (e.g., diluent controls).

DETAILED DESCRIPTION OF THE INVENTION

For the practice of one embodiment of the present invention one must first select a target cell, cell line, or infectious agent. Such a target cell can include human tumor cell lines (e.g., melanomas, lung tumor lines, renal tumor lines, colon tumor lines, prostate tumor lines, ovarian tumor lines, breast tumor lines, central nervous system tumor lines, leukemic cell lines, etc.); human fibroblasts; human leukocytes; murine tumor cell lines (e.g., P388 murine leukemia); human tumor xenografts; fresh patient derived tumor tissue; human lymphoid cell lines; cultured primary cell lines; bacteria; virus-infected cell lines (e.g., human cell lines producing human immunodeficiency virus); yeast and fungi; as well as other cell lines, strains or tumors of mammalian species.

The target cells selected for cultivation in the encapsulation device are cultivated in vitro in a culture medium appropriate for the cell line. Appropriate media known in the art include, but are not limited to: RPMI 1640; Eagles' minimal essential medium (MEM); Dulbecco's modified MEM, or others. For most cell lines the culture medium includes 10% fetal calf serum. Selected cell strains may require serum-free medium or other serum defined medium for culture. If fresh tumor tissue is used as the target, the cells are dispersed mechanically or enzymatically (using protein degrading enzyme, such as collagenase) before cultivation. The cells are cultured to maintain them in logarithmic growth as appropriate for each cell line. The cells are provided with fresh medium 24 hours prior to harvest for culture in hollow fibers.

One must then select an encapsulation device in which to cultivate the target cells in vivo. The encapsulation device can be any biocompatible, semi-permeable, implantable device. Preferred forms of macroencapsulation devices include selectively permeable hollow fibers or dialysis tubing. Suitable hollow fibers (HF) include, but are not limited to, those composed of polysulfone (PS), polyvinylidene fluoride (PVDF), cellulose acetate (CA-E), saponified cellulose ester (SCE) or polypropylene (PP). Suitable dialysis tubing (DT) includes, but is not limited to, that composed of regenerated cellulose (RC) or cellulose ester (CE). Other biocompatible, semi-permeable materials can be used in a similar format, depending upon their capacity to support cell growth. Following are the physical dimensions of some examples of macroencapsulation devices, not meant to limit the scope of possible devices to practice an embodiment of the present invention:

| Material | Supplier | Internal Diameter | Mol. Wt. Cutoff |
|---|---|---|---|
| PVDF HF | Spectrum | 0.5 mm & 1.0 mm | 300,000 & 500,000 |
| PS HF | Spectrum | 0.5 mm & 1.0 mm | 2,000; 10,000; 50,000; 100,000 |
| CA-E HF | Spectrum | 1.0 mm | unknown |
| PP HF | Cellco | .33 mm | 0.5 micron pores |
| SCE HF | Althin CD | .21–.215 mm | unknown |
| CA HF | Althin CD | .22 mm | unknown |
| RC DT | Spectrum | variable | variable |
| CE DT | Spectrum | variable | variable |

Although any semi-permeable macrocapsule can be used which permits diffusion of the test agent into the device, a preferred embodiment of the present invention utilizes a device with a molecular weight cutoff of 50,000 daltons or higher.

After an appropriate macroencapsulation device is selected, the device must be prepared for loading with the target cells. PVDF, PS and CA-E hollow fibers are prepared by autoclaving 20 minutes to sterilize, flushing with 70% ethanol solution and incubating in 70% ethanol at room temperature for a period of about 24 hours or longer. The alcohol is removed with a sterile water rinse and then the fibers are filled with tissue culture medium containing 20% fetal calf serum (for cell lines which tolerate fetal calf serum) or with other proteins (collagen, fibrinogen, etc.) which can block possible protein binding sites. Following incubation for about 12 hours or longer at 37° C., the fibers are ready to be loaded with cells or other viable culture material.

SCE and CA hollow fibers are potted together into bundles with epoxy, methacrylate glue, or other appropriate biocompatible adhesive. The fiber bundles are prepared by flushing with deionized water, then sterilized chemically with 70% ethanol. The fiber bundles are flushed with sterile water to remove the alcohol and incubated in tissue culture medium containing 20% fetal calf serum or other appropriate proteins for about 12 hours or longer at 37° C., prior to loading with cells.

The RC and CE dialysis tubing are flushed with and boiled in deionized water to remove preservatives. The tubing is cut into 3-4 cm lengths and one end is sealed with a knot, methacrylate surgical glue, or other biocompatible adhesive, thereby forming "bags". The tubing is sterilized chemically with 70% ethanol, flushed with sterile water and incubated in tissue culture medium for about 12 hours or longer at 37° C. prior to loading with cells.

After appropriate preparation, the hollow fibers or dialysis tubing "bags" are ready to receive the target cells. First, the target cells or cell lines are collected and their viability determined. The cells are prepared at a cell density appropriate to maintain cellular growth in the hollow fibers. This density varies for each cell line, and must be established for each individually. As a general rule, most cells can be cultured at $1-10 \times 10^6$ cells/ml of culture medium, although higher and lower ranges can be used.

For virus infected cells, acute infectious can be performed immediately prior to transfer of the cells into hollow fibers. Alternately, chronically infected cells may be cultured. It is also possible to prepare co-cultivations by mixing virus-infected cells and uninfected target cells prior to loading them into hollow fibers. For neoplastic cells, no infection is performed, they are simply harvested and prepared at the appropriate cell density.

After preparation, the target cells are instilled into the encapsulation device. The cells may be entrapped in agarose, extracellular matrix or other supportive materials prior to loading into the encapsulation device. Pretreatment of the encapsulation device with poly-1-lysine, collagen, fibrinogen and/or other attachment/pre-treatment agents prior to loading cells into the hollow fibers can also be used to enhance cell attachment or growth, or to prepare samples for specific tests (e.g., colony formation in agarose).

The inoculum (cells, bacteria, etc.) is transferred to sterile syringes and the hollow fibers are filled using a needle of the appropriate gauge to fit into the hollow fiber or in the case of fiber bundles a piece of sterile tubing is used to connect the syringe to the bundle. The cells are flushed into the hollow fibers by applying gentle pressure on the syringe plunger. The ends on the PVDF, PS and CA-E fibers are heat sealed with smooth jawed needle holders or other appropriate devices that have been heated to 250° F. or higher.

Individual samples of PVDF, PS and CA-E for implantation are prepared from the filled hollow fibers by heat sealing the fibers at standard intervals along the tubing. Generally, for 1.0 mm diameter hollow fibers an interval length of 2 cm is used, while the 0.5 mm diameter hollow fibers are prepared in 3 cm lengths. These lengths are workable, however, any length can be used provided in vivo implantation is feasible (e.g., samples prepared for implantation in dogs are in lengths of 10-12 cm). The SCA and CA hollow fiber bundles are sealed on the ends with methacrylate surgical glue.

For dialysis tubing "bags", filling is accomplished by transferring the inoculum into the tubing with a micropipet or a needle/syringe. The dialysis tubing "bags" are closed with methacrylate surgical glue or other biocompatible sealants. While the length of these bags is dependent on the diameter of tubing being used, lengths of 2-4 cm have been demonstrated to be effective in mice.

After filling, the macrocapsules can be implanted directly into laboratory animals (mice, rats, dogs, etc.), or they can be incubated in vitro to allow stabilization of the culture and recovery from the effects of cell manipulation (i.e., trypsinization, centrifugation, cold shock, etc.) before implantation.

Macrocapsules are preferably implanted intraperitoneally or subcutaneously, or both. Samples are implanted into the intraperitoneal cavity by anesthetizing the mice with methoxyflurane (other anesthetics could be used) and making an incision through the skin over the ventral abdomen or, in a second approach, the skin over the lateral abdominal wall. The musculature of the abdomen is incised (½ cm or smaller incision) and the hollow fibers are passed through the incision and deposited in the abdominal cavity. For ventral incisions the musculature is closed with sterile suture (silk, cat gut, polyglycolic acid, etc.) and the skin is closed in a second layer with suture, wound clips or surgical glue. For dorsal incisions, only the skin is closed (suture, wound clips, glue) as there is less risk of herniation at this site than ventrally. The mice are allowed to recover from anesthesia, with a heat source provided if recovery is slow.

For subcutaneous implants a skin incision is made over the dorsal thoracic region (nape of the neck) and the hollow fibers are passed caudally through the subcutaneous tissue. This passage is facilitated using a tumor-implantation trocar (11-16 gauge). The fibers are loaded into the distal end of the trocar which is then passed caudally through the skin incision. During withdrawal of the trocar, the fiber(s) are deposited in the subcutaneous space using the trocar stylet to push the fiber out of the trocar. The skin incision is closed using suture, would clips or surgical glue.

Generally, it is recommended that one implant the intraperitoneal fibers first, then roll the animal over and implant the subcutaneous fibers. However, the fibers can be implanted in any order.

Each recipient animal can receive a single implant (i.e., a single macrocapsule) at a single site (subcutaneous, intraperitoneal, or in a specific organ), or receive multiple implants at multiple sites (i.e., 3-6 (or more) macrocapsules implanted subcutaneously and intraperitoneally in each animal). Each macrocapsule can contain the same target cell, or each can contain a different cell or cell line, infectious agent or bacteria. In this way one can encapsulate one or more cell lines in hollow fibers, implant each fiber intraperitoneally, subcutaneously, or intra-organ in the same animal, and treat the animal with an agent to determine its effect on cells cultured in the different physiologic compartments.

After implantation, the laboratory animals are treated with the test chemotherapeutic agent on a dose and schedule appropriate for the agent being evaluated. A single chemotherapeutic agent can be used during treatment, or two or more can be combined or given to the animal simultaneously to test the effect of the combination of compounds on the target cells. The chemotherapeutic agents are administered by the intravenous, intraperitoneal, subcutaneous, oral and/or percutaneous routes on any number of schedules.

The implanted samples are allowed to remain in the host animal for an appropriate period, of time, usually about 6 days. It is possible to use alternate schedules of either longer or shorter in vivo incubation periods to arrive at the endpoint to determine activity of the agent on the target cells.

The implanted samples are then harvested at the appropriate time for in vitro evaluation of the effects of the chemotherapeutic agent(s). For antineoplastic compounds, the endpoint is determined by the quantity of viable cells present in the macrocapsule which can be determined by tests known in the art, for example, MTT dye conversion assay, neutral red dye uptake, trypan blue staining, viable cell counts, the number of colonies formed in soft agar, the capacity of the cells to recover and replicate in vitro following in vivo exposure to the test agent(s), and others.

For evaluation of antiviral agents, the endpoint is determined by the number of viable cells present in the macrocapsule, the capacity of the cells to replicate, the presence of proteins, glycoproteins, nucleic acids or other products specifically associated with the infectious agent (e.g., reverse transcriptase, nucleoprotein (HIV p24)), and/or the level of infectious material recovered from the macrocapsule.

Several experiments were run using the above described method to screen a variety of chemotherapeutic agents for effectiveness against tumor cell lines. The following examples illustrate one embodiment of the present invention, but should not be used to limit its scope.

EXAMPLE 1

PVDF hollow fibers obtained from Spectrum, with an internal diameter of 1.0 mm, and a molecular weight cutoff of 500,000 daltons were prepared as described above. These fibers were then instilled with one of the following tumor cell lines, cultivated in RPMI 1640 with 20% fetal calf serum: leukemia cell line HL60; central nervous system tumor cell line U251; ovarian tumor cell line Ovcar 3; lung tumor cell line H522 or H23; colon tumor cell line SW620 or Colo 205; melanoma cell line LOX or SK-MEL-28; or renal tumor cell line SN12K1 or SN12C. The fibers were then heat sealed with heated smooth jawed needle holders at intervals of two centimeters.

These macrocapsules were then implanted intraperitoneally into mice, which were then treated intraperitoneally with one of the following chemotherapeutic agents: methotrexate (NCI #740); vinblastine (NCI #49842); adriamycin (NCI #123127); L-PAM (NCI #241286); ellipticinium (NCI #155693); mitomycin C (NCI #26980); cyclophosphamide (NCI #26271); DTIC (NCI #45388); chlorambucil (NCI #3088); BCNU (NCI #409962); cis-platinum (NCI #119875); VP-16 (NCI #141540); actinomycin D (NCI #3053); fluorouracil (NCI #19893); or bleomycin (NCI #125066), or with a control. The control consisted of the diluent used to dissolve the chemotherapeutic agent.

After treatment with a specified dose and schedule as specified in Table 2, the mice were sacrificed and the tumor cell viability determined by MTT (3-[4,5-dimethylthiazol-2-yl]-2,5-diphenyltetrazolinum bromide) assay (Cancer Res., 51:1247 (1991)). To perform this assay, a small amount of MTT is added to a sample of cells which have been collected. MTT is bright yellow/gold in color, but is converted to MTT-formazan (dark purple color) by viable cells. The greater the amount of viable cells present, the more pronounced the color change. The color is then measured in a spectrophotometer at 540 nm, using empty hollow fibers as a blank. A cell viability measurement of the control macrocapsules is also measured, and from these measurements a percentage of treated tumor growth as compared to control growth is determined using the formula: % tumor growth in treated animals compared to control animals=100×(MTT measurement for treated cells-blank)/(MTT measurement for control cells-blank).

For the present experiments, a positive response in the hollow fiber assay was defined as a reduction in viable cells of 25% or more in the drug treated mice compared to the control mice. Therefore, if the above formula is used to determine the percentage of tumor cell growth in treated animals as compared to control animals, a value of 75 or less would indicate that the tumor cell line contained in the hollow fiber and implanted in an animal treated with a chemotherapeutic agent was negatively affected (cell growth inhibited compared to control). Values of 76 or greater indicate that the tumor cells did not respond well to the tested agent.

The results for several experiments performed using PVDF hollow fiber encapsulated tumor cell lines, implanted intraperitoneally, are contained in Table 1. The dosage and dosing schedules used in these experiments are listed in Table 2. The Q2D X 3 schedule indicates treatment with the indicated drug every two days (every other day) for a total of three infusions; QD×5 indicates daily infusion for five days; Q8H×2 indicates infusion every eight hours, twice a day.

Table 1 indicates that by using the method of the present invention, one can easily screen potential chemotherapeutic agents for effectiveness against tumor cell growth. Column one of Table 1 lists the agents screened; column two gives the National Cancer Institute number assigned to each agent (NCI#); column three gives the experiment number which corresponds to experiment numbers in Table 2; and column four gives the dose administered in mg/kg/injection.

EXAMPLE 2

In the same test animals of Example 1, PVDF hollow fibers containing the same tumor cell lines as in Example 1 above were simultaneously implanted subcutaneously. These animals were tested using the same chemotherapeutic agents and dose schedules as in Example 1, or were treated with diluent (control). The percent growth of the subcutaneously implanted tumor cells in treated animals compared to control animals was determined. The results are contained in Table 3.

EXAMPLE 3

In other experiments, the tumor cell lines described in Example 1 were encapsulated in PS hollow fibers. The PS hollow fibers were obtained from Spectrum, and had an internal diameter of 0.5 mm and a molecular weight cutoff of 50,000 daltons. These fibers were heat sealed and separated into macrocapsules three centimeters in length. These PS encapsulated tumor cells were implanted intraperitoneally in mice, which were then treated intraperitoneally with one of the chemotherapeutic agents listed in Example 1, or were treated with diluent (control). The dosage schedules for these experiments are contained in Table 2. The percent growth of tumor cells in treated animals compared to control animals was determined. The results are contained in Table 4.

It has been shown that the method of the present invention is useful in evaluating the efficacy of chemotherapeutic agents against one or more targets (i.e. tumor types, viruses, bacterial strains, etc.) at one or more implant sites (subcutaneous, intraperitoneal) by comparing the endpoint results obtained in animals treated with the test agents to the results obtained in animals treated with placebo (e.g., diluent controls). The advantages of this system over the classical antitumor animal models includes one or more of the following: (1) the requirement for a smaller amount of test agent to assess preliminary in vivo efficacy, for example, to screen a drug dosed at 100 mg/kg the classical model would require a total of 160 mg of test agent, while using the method of the present invention would require 35 mg of test agent, (2) the rapid turn-around time (10 day assay), (3) the ability to test potential activity against multiple tumor types simultaneously in the same experimental animals, for example, implanting six macrocapsules each containing a different cell line, (4) a reduction in the number of experimental animals required for assessing efficacy (the classical model requires 30 animals while the present method uses 6), (5) the possibility of assessing multiple treatment schedules in a short time frame, (6) the ability to recover the entire implant, (7) the lack of contamination of the implanted cells by host cells, and (8) the ability to screen a test agent against target cells cultivated in various physiologic compartments in the same laboratory animal, for example, implanting macrocapsules containing target cells intraperitoneally, subcutaneously and intra-organ in the same animal and subjecting the animal to a test agent. These same advantages exist for assessing antiviral agents and have the added benefit of allowing short-term replication of viruses in susceptible cell lines in a host (i.e., mouse, rat, dog, etc.) which does not normally support replication of the viruses.

Additionally, the present method can be used in transgenic animals to determine the effect of a transgene or protein product thereof on a target cell line. Or, encapsulated target cells can be implanted in humans for screening of test agents. Further, by encapsulating target cells and screening them against a test agent in vivo, then harvesting the cells, re-cultivating them and re-screening them by repeating the present method, it is possible to assess the regrowth potential of cells surviving treatment and then determine their susceptibility to a second treatment with the same or alternate anticancer agents.

The invention has been described in detail with particular reference to a preferred embodiment thereof, but it will be understood that the invention is capable of other and different embodiments. As is readily apparent to those skilled in the art, variations and modifications can be affected within the spirit and scope of the invention. Accordingly, the foregoing disclosure and description are for illustrative purposes only, and do not in any way limit the invention, which is defined only by the claims.

TABLE 1

Normalized MTT Reading: 100 × (value-blank)/(control-blank)

| PVDF Tubing: Fibers Implanted IP | | | | Leuk. | CNS | Ovar. | nsLung | | Colon | | Melan. | Renal | |
|---|---|---|---|---|---|---|---|---|---|---|---|---|---|
| Drug: | NCI# | expt# | dose | HL60 | U251 | Ovcar3 | H522 | H23 | SW620 | Colo205 | LOX | Sk-Mel-28 Sn12K1 | SN12C |
| Methotrexate | 740 | 48 | 30 | 48 | | 70 | | | | | | 45 | |
| Methotrexate | 740 | 3 | 30 | | | | | | 90 | | | 105 | 50 |
| Vinblastine | 49842 | 48 | 0.75 | −2 | | 133 | | | | | | 4 | |
| Vinblastine | 49842 | 22 | 2 | | | | | 36 | | | | 72 | 18 |
| Vinblastine | 49842 | 27 | 0.75 | | | | | 14 | | | | 73 | 53 |
| Vinblastine | 49842 | 37 | 0.75 | | 37 | | | | 35 | | 16 | | |
| Adriamycin | 123127 | 48 | 4 | 5 | | 24 | | | | | | 2 | |
| Adriamycin | 123127 | 31 | 4 | | | | | 15 | | | | 109 | 38 |
| L-PAM | 241286 | 48 | 6 | −2 | | | | 23 | | | | 25 | |
| L-PAM | 241286 | 27 | 6 | | | | | 58 | | | | 172 | 51 |
| L-PAM | 241286 | 37 | 6 | | 55 | | | | 61 | | 38 | | |
| Ellipticinium | 155693 | 48 | 25 | | 25 | | | | | | | 51 | |
| Mitomycin C | 26980 | 51 | 2.5 | 51 | | 32 | 21 | | 38 | 42 | | 39 | |
| Mitomycin C | 26980 | 64 | 1.67 | | | | | 32 | | | | | |
| Mitomycin C | 26980 | 31 | 2.5 | | | | | 1 | | | 60 | | 54 |
| Cyclophosphamide | 26271 | 51 | 60 | 129 | | 108 | | | | | | 105 | |
| Cyclophosphamide | 26271 | 31 | 60 | | | | | 83 | | | | 105 | 68 |
| DTIC | 45388 | 51 | 250 | 146 | | 103 | | | | | | 85 | |
| DTIC | 45388 | 27 | 250 | | | | | 108 | | | | 81 | 129 |
| DTIC | 45388 | 37 | 250 | | 63 | | | | 57 | | 35 | | |
| Chlorambucil | 3088 | 51 | 25 | 19 | | 71 | | | | | | 52 | |
| Chlorambucil | 3088 | 22 | 25 | | | | | 6 | | | | 153 | 6 |
| BCNU | 409962 | 51 | 25 | 141 | | | 86 | | 94 | | | | |
| BCNU | 409962 | 31 | 10 | | | | | 71 | | | | 96 | 60 |
| Cis-Platinum | 119875 | 51 | 3.5 | 32 | | | 56 | | | 67 | | | |
| Cis-Platinum | 119875 | 37 | 5 | | 26 | | | | 43 | | 18 | | |
| Cis-Platinum | 119875 | 27 | 5 | | | | | 56 | | | | 69 | 65 |
| VP-16 | 141540 | 22 | 50 | | | | | 75 | | | | 132 | 34 |
| Actinomycin D | 3053 | 27 | 0.2 | | | | | 1 | | | | 83 | 37 |
| Actinomycin D | 3053 | 37 | 0.2 | 4 | | | | | 20 | | 1 | | |
| 5-Fluorouracil | 19893 | 27 | 40 | | | | | 167 | | | | 83 | 88 |
| 5-Fluorouracil | 19893 | 37 | 40 | | 74 | | | | 76 | | 50 | | |
| Bleomycin | 125066 | 31 | 10 | | | | | 82 | | | | 100 | 113 |

| Expt # | NCI # | Dose | Schedule |
|---|---|---|---|
| 14 | 740 | 40 mg/kg/inj | Q2D × 3, start Day 1 |
|  | 26271 | 60 mg/kg/inj | Q2D × 3, start Day 1 |
|  | 26980 | 2.5 mg/kg/inj | Q2D × 3, start Day 1 |
| 17 | 740 | 40 mg/kg/inj | Q2D × 3, start Day 1 |
|  | 26271 | 60 mg/kg/inj | Q2D × 3, start Day 1 |
|  | 26980 | 2.5 mg/kg/inj | Q2D × 3, start Day 1 |
| 19 | 740 | 40 mg/kg/inj | Q2D × 3, start Day 1 |
|  | 26271 | 60 mg/kg/inj | Q2D × 3, start Day 1 |
|  | 26980 | 2.5 mg/kg/inj | Q2D × 3, start Day 1 |
| 22 | 3088 | 25 mg/kg/inj | Q2D × 3, start Day 1 |
|  | 49842 | 2 mg/kg/inj | Q2D × 3, start Day 1 |
|  | 141540 | 50 mg/kg/inj | Q2D × 3, start Day 1 |
| 27 | 3053 | 0.2 mg/kg/inj | Q2D × 3, start Day 1 |
|  | 241286 | 6 mg/kg/inj | Q2D × 3, start Day 1 |
|  | 19893 | 40 mg/kg/inj | Q2D × 3, start Day 1 |
|  | 45388 | 250 mg/kg/inj | Q2D × 3, start Day 1 |
|  | 49842 | 0.75 mg/kg/inj | Q2D × 3, start Day 1 |
|  | 119875 | 5 mg/kg/inj | Q2D × 3, start Day 1 |
| 31 | 740 | 30 mg/kg/inj | Q2D × 3, start Day 1 |
|  | 26271 | 60 mg/kg/inj | Q2D × 3, start Day 1 |
|  | 26980 | 2.5 mg/kg/inj | Q2D × 3, start Day 1 |
|  | 123127 | 4 mg/kg/inj | Q2D × 3, start Day 1 |
|  | 125066 | 10 mg/kg/inj | Q2D × 3, start Day 1 |
|  | 409962 | 10 mg/kg/inj | Q2D × 3, start Day 1 |
| 37 | 3053 | 0.2 mg/kg/inj | Q2D × 3, start Day 1 |
|  | 241286 | 6 mg/kg/inj | Q2D × 3, start Day 1 |
|  | 19893 | 40 mg/kg/inj | Q2D × 3, start Day 1 |
|  | 45388 | 250 mg/kg/inj | Q2D × 3, start Day 1 |
|  | 49842 | 0.75 mg/kg/inj | Q2D × 3, start Day 1 |
|  | 119875 | 5 mg/kg/inj | Q2D × 3, start Day 1 |
| 44 | 740 | 30 mg/kg/inj | Q2D × 3, start Day 1 |
|  | 26271 | 60 mg/kg/inj | Q2D × 3, start Day 1 |
|  | 26980 | 2.5 mg/kg/inj | Q2D × 3, start Day 1 |
|  | 123127 | 4 mg/kg/inj | Q2D × 3, start Day 1 |
|  | 125066 | 10 mg/kg/inj | Q2D × 3, start Day 1 |
|  | 409962 | 10 mg/kg/inj | Q2D × 3, start Day 1 |
| 48 | 740 | 30 mg/kg/inj | Q2D × 3, start Day 1 |
|  | 3053 | 0.2 mg/kg/inj | Q2D × 3, start Day 1 |
|  | 49842 | 0.75 mg/kg/inj | Q2D × 3, start Day 1 |
|  | 123127 | 4 mg/kg/inj | Q2D × 3, start Day 1 |
|  | 241286 | 6 mg/kg/inj | Q2D × 3, start Day 1 |
|  | 155693 | 25 mg/kg/inj | Q2D × 3, start Day 1 |
| 51 | 26980 | 2.5 mg/kg/inj | Q2D × 3, start Day 1 |
|  | 26271 | 60 mg/kg/inj | Q2D × 3, start Day 1 |
|  | 45388 | 250 mg/kg/inj | Q2D × 3, start Day 1 |
|  | 119875 | 3.5 mg/kg/inj | Q2D × 3, start Day 1 |
|  | 409962 | 10 mg/kg/inj | Q2D × 3, start Day 1 |
|  | 3088 | 25 mg/kg/inj | Q2D × 3, start Day 1 |
| 64 | 26980 | 1 mg/kg/inj | QD × 5, start Day 1 |
|  | 26980 | 0.5 mg4kg/inj | QD × 5, start Day 1 |
|  | 26980 | 0.5 mg/kg/inj | Q8H × 2, Days 1-5 |
|  | 26980 | 1.67 mg/kg/inj | Q2D × 3, start Day 1 |
|  | 26980 | 0.835 mg/kg/inj | Q2D × 3, start Day 1 |
|  | 26980 | 5 mg/kg/inj | QD × 1, Day 1 |

TABLE 3

Normalized MTT Reading: 100 × (value-blank)/(control-blank)

| PVDF Tubing: Fibers Implanted SC | | | | Leuk. | CNS | Ovar. | nsLung | | Colon | | Melan. | | Renal | |
|---|---|---|---|---|---|---|---|---|---|---|---|---|---|---|
| Drug: | NCI# | expt# | dose | HL60 | U251 | Ovcar3 | H522 | H23 | SW620 | Colo205 | LOX | Sk-Mel-28 | Sn12K1 | SN12C |
| Methotrexate | 740 | 48 | 30 | 22 |  | 91 |  |  |  |  |  |  | 65 |  |
| Methotrexate | 740 | 31 | 30 |  |  |  |  | 91 |  |  |  | 81 |  | 49 |
| Vinblastine | 49842 | 48 | 0.75 | 48 |  | 87 |  |  |  |  |  |  | 95 |  |
| Vinblastine | 49842 | 22 | 2 |  |  |  |  |  | 105 |  |  | 153 |  | 282 |
| Vinblastine | 49842 | 27 | 0.75 |  |  |  |  | 118 |  |  |  | 83 |  | 96 |
| Vinblastine | 49842 | 37 | 0.75 |  | 101 |  |  |  | 163 |  | 41 |  |  |  |
| Adriamycin | 123127 | 48 | 4 | 88 |  | 110 |  |  |  |  |  |  | 54 |  |
| Adriamycin | 123127 | 31 | 4 |  |  |  |  | 82 |  |  |  | 59 |  | 103 |
| L-PAM | 241286 | 48 | 6 | 37 |  |  |  | 92 |  |  |  |  | 77 |  |
| L-PAM | 241286 | 27 | 6 |  |  |  |  | 131 |  |  |  | 121 |  | 109 |
| L-PAM | 241286 | 37 | 6 |  | 85 |  |  |  | 111 |  | 142 |  |  |  |
| Ellipticinium | 155693 | 48 | 25 | 99 | 88 |  |  |  |  |  |  |  | 98 |  |
| Mitomycin C | 26980 | 51 | 2.5 | 42 |  | 62 | 67 |  | 75 | 47 |  |  | 65 |  |
| Mitomycin C | 26980 | 64 | 1.67 |  |  |  |  | 48 |  |  |  |  |  |  |
| Mitomycin C | 26980 | 31 | 2.5 |  |  |  |  | 23 |  |  |  | 81 |  | 51 |
| Cyclophosphamide | 26271 | 51 | 60 | 102 |  | 95 |  |  |  |  |  |  | 120 |  |
| Cyclophosphamide | 26271 | 31 | 60 |  |  |  |  | 60 |  |  |  | 63 |  | 36 |
| DTIC | 45388 | 51 | 250 | 73 |  | 65 |  |  |  |  |  |  | 76 |  |
| DTIC | 45388 | 27 | 250 |  |  |  |  | 81 |  |  |  | 117 |  | 100 |
| DTIC | 45388 | 37 | 250 |  | 51 |  |  |  | 71 |  | 19 |  |  |  |
| Chlorambucil | 3088 | 51 | 25 | 15 |  | 65 |  |  |  |  |  |  | 61 |  |
| Chlorambucil | 3088 | 22 | 25 |  |  |  |  | 83 |  |  |  | 157 |  | 297 |
| BCNU | 409962 | 51 | 25 | 74 |  |  | 119 |  | 108 |  |  |  |  |  |
| BCNU | 409962 | 31 | 10 |  |  |  |  | 86 |  |  |  | 66 |  | 51 |
| Cis-Platinum | 119875 | 51 | 3.5 | 39 |  |  | 103 |  |  | 80 |  |  |  |  |
| Cis-Platinum | 119875 | 37 | 5 |  | 63 |  |  |  | 73 |  | 54 |  |  |  |
| Cis-Platinum | 119875 | 27 | 5 |  |  |  |  | 27 |  |  |  | 137 |  | 83 |
| VP-16 | 141540 | 22 | 50 |  |  |  |  | 88 |  |  |  | 189 |  | 205 |
| Actinomycin D | 3053 | 27 | 0.2 |  |  |  |  | 99 |  |  |  | 121 |  | 83 |
| Actinomycin D | 3053 | 37 | 0.2 |  | 93 |  |  |  | 127 |  | 80 |  |  |  |
| 5-Fluorouracil | 19893 | 27 | 40 |  |  |  |  | 82 |  |  |  | 113 |  | 123 |
| 5-Fluorouracil | 19893 | 37 | 40 |  | 80 |  |  |  | 125 |  | 99 |  |  |  |
| Bleomycin | 125066 | 31 | 10 |  |  |  |  | 89 |  |  |  | 64 |  | 78 |

TABLE 4

| PS Tubing: Fibers Implanted IP | | | | Normalized MTT Reading: 100 × (value-blank)/(control-blank) Cell Type | | | | | | | | | |
|---|---|---|---|---|---|---|---|---|---|---|---|---|---|
| | | | | Leuk. | CNS | Ovar. | nsLung | | Colon | | Melan. | Renal | |
| Drug: | NCI# | expt# | dose | HL60 | U251 | Ovcar3 | H522 | H23 | SW620 | Colo205 | LOX | Sk-Mel-28 | Sn12K1 | SN12C |
| Methotrexate | 740 | 48 | 30 | 42 | | 63 | | | | | | | 41 | |
| Methotrexate | 740 | 31 | 30 | | | | | 90 | | | | 176 | | 33 |
| Methotrexate | 740 | 14 | 40 | | | | | 129 | | | | | | |
| Methotrexate | 740 | 17 | 40 | | | | | 101 | | | | | | |
| Methotrexate | 740 | 19 | 40 | | | | | 100 | | | | | | |
| Vinblastine | 49842 | 48 | 0.75 | 2 | | −11 | | | | | | | −2 | |
| Vinblastine | 49842 | 27 | 0.75 | | | | | 153 | | | | 17 | | |
| Vinblastine | 49842 | 37 | 0.75 | | 21 | | | | 34 | | 6 | | | |
| Adriamycin | 123127 | 48 | 4 | −3 | | −7 | | | | | | | −2 | |
| Adriamycin | 123127 | 31 | 4 | | | | | 2 | | | | 88 | | 27 |
| L-PAM | 241286 | 48 | 6 | −4 | | | | −6 | | | | | 35 | |
| L-PAM | 241286 | 27 | 6 | | | | | 7 | | | | 84 | | |
| L-PAM | 241286 | 37 | 6 | | 55 | | | | 28 | | 14 | | | |
| Ellipticinium | 155693 | 48 | 25 | 130 | 1 | | | | | | | | 42 | |
| Mitomycin C | 26980 | 51 | 2.5 | −5 | | 3 | −8 | | | | | | 31 | |
| Mitomycin C | 26980 | 64 | 1.67 | | | | | 0 | | | | | | |
| Mitomycin C | 26980 | 31 | 2.5 | | | | | −1 | | | | 53 | | 51 |
| Mitomycin C | 26980 | 14 | 2.5 | | | | | 2 | | | | | | |
| Mitomycin C | 26980 | 17 | 2.5 | | | | | −4 | | | | | | |
| Mitomycin C | 26980 | 19 | 2.5 | | | | | 2 | | | | | | |
| Cyclophosphamide | 26271 | 51 | 60 | 64 | | 125 | | | | | | | 110 | |
| Cyclophosphamide | 26271 | 31 | 60 | | | | | 44 | | | | 171 | | 53 |
| Cyclophosphamide | 26271 | 14 | 60 | | | | | 49 | | | | | | |
| Cyclophosphamide | 26271 | 17 | 60 | | | | | 8 | | | | | | |
| Cyclophosphamide | 26271 | 19 | 60 | | | | | 19 | | | | | | |
| DTIC | 45388 | 51 | 250 | 90 | | 248 | | | | | | | 70 | |
| DTIC | 45388 | 27 | 250 | | | | | 90 | | | | 90 | | |
| DTIC | 45388 | 37 | 250 | | 47 | | | | 33 | | 27 | | | |
| Chlorambucil | 3088 | 51 | 25 | 3 | | 44 | | | | | | | 51 | |
| Chlorambucil | 3088 | 22 | 25 | | | | | 38 | | | | 112 | | 55 |
| RCNU | 409962 | 51 | 25 | 46 | | | 68 | | 212 | | | | | |
| RCNU | 409962 | 31 | 10 | | | | | 74 | | | | 1224 | | 40 |
| Cis-Platinum | 119875 | 51 | 3.5 | −5 | | | 9 | | | 46 | | | | |
| Cis-Platinum | 119875 | 37 | 5 | | 12 | | | | 17 | | 7 | | | |
| Cis-Platinum | 119875 | 27 | 5 | | | | | 33 | | | | 66 | | |
| VP-16 | 141540 | 22 | 50 | | | | | 61 | | | | 108 | | 55 |
| Actinomycin D | 3053 | 27 | 0.2 | | | | | 2 | | | | 39 | | |
| Actinomycin D | 3053 | 37 | 0.2 | | 7 | | | | 1 | | 1 | | | |
| 5-Fluorouracil | 19893 | 27 | 40 | | | | | 133 | | | | 81 | | |
| 5-Fluorouracil | 19893 | 37 | 40 | | 95 | | | | 91 | | 9 | | | |
| Bleomycin | 125066 | 31 | 10 | | | | | 53 | | | | 92 | | 105 |

We claim:

1. A method of screening chemotherapeutic agents in vivo comprising the steps of:
   (a) implanting into a mammal at least one biocompatible, tubular, semi-permeable encapsulation device containing a group of target cells within an interior of said device wherein said device has a molecular weight cut off of greater than 50,000 daltons and said device is comprised of polyvinylidine fluoride;
   (b) treating said mammal with at least one chemotherapeutic agent; and
   (c) evaluating said target cells for reaction to the at least one chemotherapeutic agent.

2. A method of screening chemotherapeutic agents in vivo, comprising the steps of:
   (a) implanting into a mammal at least one biocompatible, tubular, semi-permeable encapsulation device containing a group of target cells within an interior of said device, wherein said device has a molecular weight cutoff of greater than 100,000 daltons;
   (b) treating said mammal with at least one chemotherapeutic agent; and
   (c) evaluating said target cells for reaction to the at least one chemotherapeutic agent.

3. A method of screening chemotherapeutic agents, in vivo comprising the steps of:
   (a) implanting into a mammal at least one biocompatible, tubular, semi-permeable encapsulation device, containing a group of target cells within an interior of said device, said device being comprised of polyvinylidene fluoride;
   (b) treating said mammal with at least one chemotherapeutic agent; and
   (c) evaluating said target cells for reaction to the at least one chemotherapeutic agent.

4. The method of claim 1, 2, or 3, wherein said biocompatible, semi-permeable tubular encapsulation device has a molecular weight cutoff of less than about 500,000 daltons.

5. The method of claims 1, 2, or 3, wherein a multiplicity of encapsulation devices is implanted.

6. The method of claims 1, 2, or 3, wherein said implanting step comprises subcutaneous, intraperitoneal, or intraorgan implantation.

7. The method of claims 1, 2, or 3, wherein at least one encapsulation device is implanted subcutaneously and at least one encapsulation device is implanted intraperitoneally.

8. The method of claims 1, 2, or 3, wherein said encapsulation devices are each instilled with the same target cells.

9. The method of claims 1, 2, or 3, wherein said encapsulation devices are each instilled with different target cells.

10. The method of claims 1, 2, or 3 wherein said target cells are selected from the group consisting of tumor cells, fibroblasts, leukocytes, lymphoid cells, cultured primary cells, bacteria, virus-infected cells, yeast and fungi.

11. The method of claim 1, 2, or 3, wherein said target cells are selected from the group consisting of melanomas, lung tumor lines, prostate tumor lines, ovarian tumor lines, breast tumor lines, renal tumor lines, colon tumor lines, central nervous system tumor lines, leukemic or lymphoma cell lines, tumor xenografts and fresh patient derived tumor tissue.

12. The method of claim 1, 2, or 3, wherein said target cells are infected with a virus incapable of replication in said mammal.

13. The method of claims 1, 2, or 3, wherein said mammal is selected from the group consisting of mouse, rat, hamster, guinea pig, rabbit, cat, and dog.

14. A method of screening chemotherapeutic agents in vivo comprising the steps of:
   (a) implanting into a mammal at least one biocompatible, tubular, semi-permeable encapsulation device containing a group of target cells infected with a virus;
   (b) treating said mammal with at least one chemotherapeutic agent; and
   (c) evaluating said viral infection in said target cells for effect by the at least one chemotherapeutic agent.

15. The method of claim 14, wherein said biocompatible, semi-permeable encapsulation device has a molecular weight cutoff of between about 50,000 daltons and about 500,000 daltons.

16. The method of claims 14, wherein a multiplicity of encapsulation devices is implanted.

17. The method of claim 14, wherein at least one encapsulation device is implanted subcutaneously and at least one encapsulation device is implanted intraperitoneally.

18. The method of claim 14 wherein said implanting step comprises subcutaneous, intraperitoneal, or intraorgan implantation.

19. The method of claim 14 wherein said encapsulation devices are each instilled with the same target cell.

20. The method of claims 14 wherein said encapsulation devices are each instilled with different target cells.

21. The method of claim 14 wherein said target cells are selected from the group consisting of tumor cells, fibroblasts, leukocytes, lymphoid cells, cultured primary cells, bacteria, yeast, and fungi.

22. The method of claim 14 wherein said target cells are selected from the group consisting of said tumor cells are selected from the group consisting of melanomas, lung tumor lines, prostate tumor lines, ovarian tumor lines, breast tumor lines, renal tumor lines, colon tumor lines, central nervous system tumor lines, leukemic or lymphoma cell lines, tumor xenografts and fresh patient derived tumor tissue.

23. The method of claim 14 wherein said mammal is selected from the group consisting of mouse, rat, hamster, guinea pig, rabbit, cat and dog.

24. The method of claim 14 wherein said target cell is infected with a virus incapable of replication in said mammal.

25. The method of claim 14 wherein said device is comprised of a material selected from the group consisting of polysulfone, polyvinylidene fluoride, cellulose acetate, saponified cellulose ester, polypropylene, polyamide, polyvinyl chloride, and acrylic co-polymer.

26. The method of claim 25 wherein said device is comprised of polyvinylidene fluoride.

27. The method of claim 14 wherein said target cell is a retrovirus infected cell.

28. The method of claim 27 wherein said retrovirus-infected cell comprises the human immunodeficiency virus.

* * * * *